(12) United States Patent  
Kerr

(10) Patent No.: US 8,061,473 B1
(45) Date of Patent: Nov. 22, 2011

(54) PASSIVE PERSONAL VOCAL MONITOR

(75) Inventor: Steven D. Kerr, Marietta, GA (US)

(73) Assignee: Simply Sound, Marietta, GA (US)

(*) Notice: Subject to any disclaimer, the term of this patent is extended or adjusted under 35 U.S.C. 154(b) by 0 days.

(21) Appl. No.: 12/853,404

(22) Filed: Aug. 10, 2010

(51) Int. Cl.
A61B 7/02 (2006.01)
A61F 2/20 (2006.01)
H03G 3/00 (2006.01)
H04R 5/02 (2006.01)
H04R 29/00 (2006.01)

(52) U.S. Cl. ......... 181/135; 381/58; 381/71.6; 381/104; 381/309

(58) Field of Classification Search ............. 181/135; 381/104, 58, 71.6, 309
See application file for complete search history.

(56) References Cited

U.S. PATENT DOCUMENTS

| 4,893,344 | A  | * | 1/1990  | Tragardh et al. | 381/381 |
| 5,298,692 | A  | * | 3/1994  | Ikeda et al. | 181/135 |
| 5,327,506 | A  | * | 7/1994  | Stites, III | 381/355 |
| 5,373,555 | A  | * | 12/1994 | Norris et al. | 379/430 |
| 5,613,222 | A  | * | 3/1997  | Guenther | 455/575.2 |
| 5,664,014 | A  | * | 9/1997  | Yamaguchi et al. | 379/430 |
| 5,675,658 | A  | * | 10/1997 | Brittain | 381/72 |
| 5,812,659 | A  | * | 9/1998  | Mauney et al. | 379/430 |
| 6,078,825 | A  | * | 6/2000  | Hahn et al. | 455/569.2 |
| 6,181,801 | B1 | * | 1/2001  | Puthuff et al. | 381/380 |
| 6,625,293 | B1 | * | 9/2003  | Nageno et al. | 381/362 |
| 7,551,940 | B2 | * | 6/2009  | Paulson et al. | 455/550.1 |
| 2002/0131585 | A1 | * | 9/2002 | Jones et al. | 379/431 |
| 2006/0183964 | A1 | * | 8/2006 | Kehoe | 600/23 |
| 2008/0170724 | A1 | * | 7/2008 | Cancelmo | 381/104 |
| 2009/0074196 | A1 | * | 3/2009 | Tiodor et al. | 381/58 |
| 2009/0092271 | A1 | * | 4/2009 | Fay et al. | 381/328 |
| 2009/0208047 | A1 | * | 8/2009 | Ngia et al. | 381/338 |
| 2009/0209304 | A1 | * | 8/2009 | Ngia et al. | 455/575.2 |
| 2010/0041447 | A1 | * | 2/2010 | Graylin | 455/575.2 |
| 2010/0195842 | A1 | * | 8/2010 | Sibbald | 381/71.6 |
| 2010/0215198 | A1 | * | 8/2010 | Ngia et al. | 381/309 |
| 2010/0284545 | A1 | * | 11/2010 | Dietz | 381/58 |

* cited by examiner

Primary Examiner — Elvin G Enad
Assistant Examiner — Christina Russell
(74) Attorney, Agent, or Firm — Womble Carlyle Sandridge & Rice, LLC

(57) ABSTRACT

A passive personal vocal monitor is described for enhancing the sound of a singer's voice to the singer during a performance. The monitor has an earpiece with a nipple configured to be disposed snuggly within the singer's ear and having an internal channel terminating in an open end adjacent the singer's eardrum. A tubular acoustic waveguide extends from the earpiece to an open end that is positionable adjacent the singer's mouth when the nipple is in the singer's ear. A canal in the earpiece couples the tubular waveguide to the channel of the nipple so that sounds of the singer's voice are conveyed along the waveguide and to the user's eardrum during a singing performance. An adjustable ambient sound inlet is provided on the earpiece so that a singer may admit a desired amount of ambient sound to be mixed with his voice as he sings.

19 Claims, 2 Drawing Sheets

PASSIVE PERSONAL VOCAL MONITOR

TECHNICAL FIELD

This disclosure relates generally to singing and more specifically to vocal monitors used by singers to hear their voices clearly amidst high levels of background sounds.

BACKGROUND

A singer in a band, choir, or other musical group often finds it difficult to hear his (which should be read "his or her" throughout this disclosure) own voice clearly amidst the background sounds of drums, electrically amplified instruments, and/or fellow singers. Without this feedback, the singer's voice can and often is off-pitch. Further, a singer can find it difficult to control the dynamics of his voice in an environment with high levels of background sound, and commonly finds himself screaming or belting out a song rather than singing it in a controlled manner. The ultimate result is a poor performance by the singer, which he often does not realize until listening back to a recording of the performance.

Vocal monitors exist to provide singers on stage with the ability to hear themselves over the loud background sounds of a band or fellow singers. Such monitors include, for example, stage monitors, often referred to as wedges, which are loudspeakers placed on the floor facing up at the singer. The singer's voice is amplified and reproduced through the stage monitors to allow the singer to hear himself more clearly. A problem with stage monitors is that they are large, heavy, expensive, and require electronic amplifiers and mixers which generally must be operated by a sound engineer, who may be dedicated to providing custom vocal mixes to a number of performances. Further, the loud amplified vocal sounds produced by the monitors can interfere with the overall house mix of the band's public address (PA) system, often making it muddy and difficult to control by a front-of-house (FOH) sound engineer. This is particularly true in smaller venues where sounds produced by stage monitors reflect off of walls back toward an audience.

Spot monitors are similar to stage monitors, except that they are smaller loudspeakers that usually are mounted on a stand facing the singer. While spot monitors are indeed smaller and lighter, they nevertheless require electronic amplification and mixers for operation and can also interfere with the overall house mix of the band. More recently, in-ear vocal monitors have become available. These are very small sophisticated audio transducers disposed within ear buds that a singer can insert into his ear during a performance. Amplified sounds of the singer's voice and perhaps other sounds are reproduced by the transducers directly within the singer's ear so that the singer has a personal monitor mix that cannot interfere with the overall sound of a band or vocal group. While in-ear monitors have proven somewhat successful, they nevertheless can be exceedingly expensive due to their high degree of electronic sophistication. They generally operate on small batteries, which can die or fail during a performance with dire results. Further, in-ear monitors require amplification equipment, mixing equipment, and the like, which generally must be operated by a dedicated sound engineer.

A need exists for a vocal monitor for use by singers in bands, choirs, and other vocal groups that is simple to use, operates without electronics or batteries, inexpensive, controllable by the singer himself without a sound engineer, and that cannot interfere with the overall sound mix of the band or group. It is to the provision of such a vocal monitor that this disclosure if primarily directed.

SUMMARY

Briefly described, a passive personal vocal monitor comprises an earpiece configured to fit snuggly in the ear of a singer. The earpiece has an internal canal that terminates at an open end within the singer's ear near his eardrum. A tubular acoustic waveguide is coupled to the earpiece and extends along the singer's cheek to a position near his mouth, where the waveguide terminates in a generally open end. An internal passageway of the waveguide is in sonic communication with the internal canal of the earpiece. When the singer sings, acoustic vibrations from his voice impinge upon the open end of the waveguide and create corresponding sound pressure waves in the column of air within the waveguide. These pressure waves are transmitted along the internal passageway of the waveguide to the canal of the earpiece. The acoustic pressure waves ultimately emerge from the open end of the canal and impinge upon the eardrum of the singer. Thus, the sound of the singer's voice is transmitted directly to his eardrum so that he is able to hear himself clearly and in real time. The monitor may be provided with a baffle on the earpiece that can be selectively opened and closed to allow increased or decreased levels of ambient sound into the internal canal of the earpiece. By adjusting the baffle, a singer can create a personal vocal mix (i.e. a relative volume of his own voice with ambient sounds) heard through the monitor, and this mix can be adjusted as necessary by the singer by adjusting the baffle as desired.

Thus, a personal vocal monitor is provided that is small, lightweight, inexpensive, does not require electronics, batteries, amplification or ancillary mixing equipment, and that eliminates the need for a monitor engineer to create and control the monitor mixes of various singers. These and other features, aspects, and advantages will be appreciated better upon review of the detailed description set forth below taken in conjunction with the accompanying drawing figures, which are briefly described as follows.

BRIEF DESCRIPTION OF THE DRAWINGS

FIG. 3 is a plan view of the earpiece of the monitor with a cap portion removed to illustrate one embodiment of a mix control baffle according to the disclosure.

DETAILED DESCRIPTION

Figure 1:
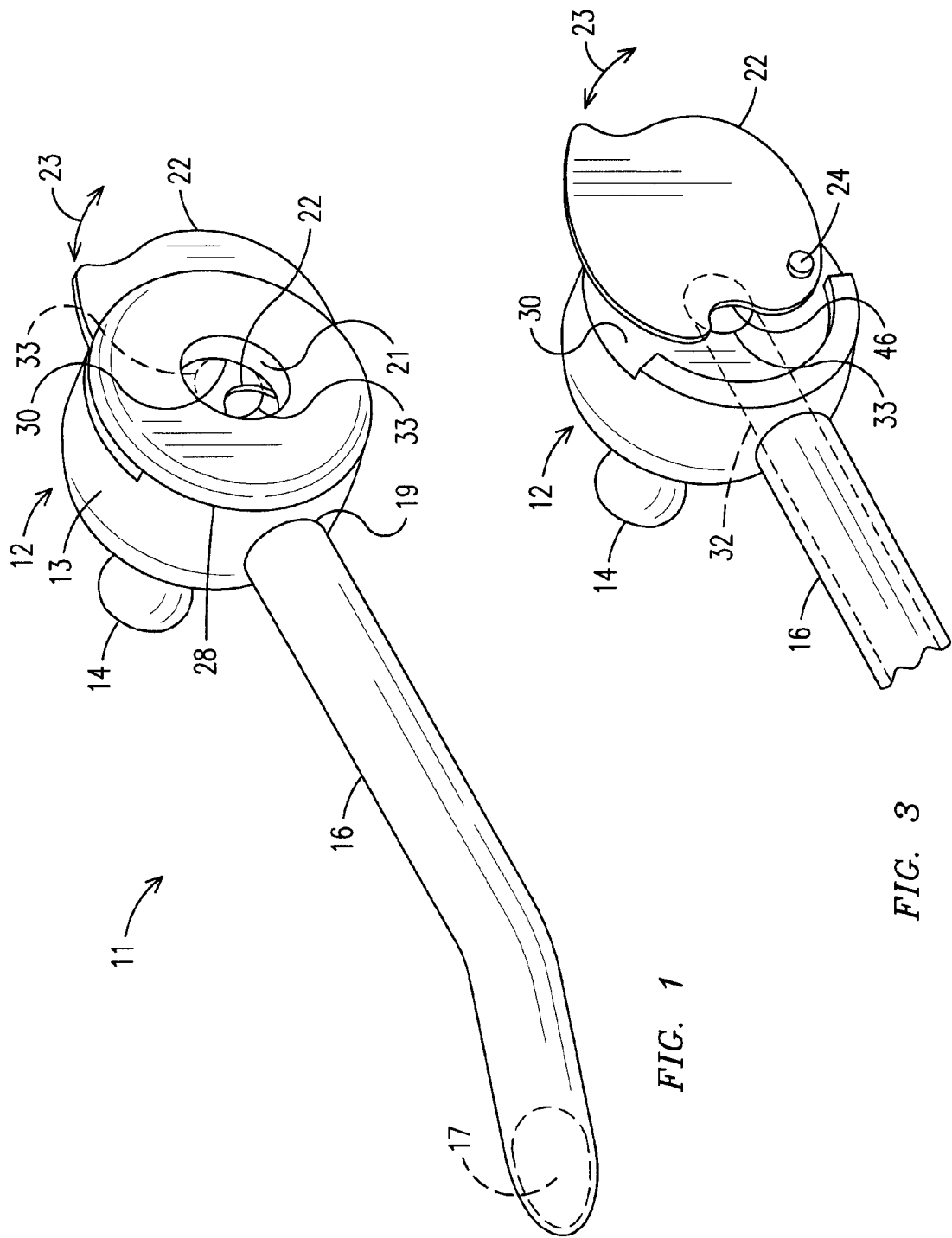
FIG. 1 is a perspective view illustrating a passive personal vocal monitor according to this disclosure.

Referring now in more detail to the drawing figures, wherein like reference numerals indicate like parts throughout the several views, FIG. 1 illustrates a passive personal vocal monitor that embodies principles of the invention in one possible embodiment thereof. The monitor 11 includes an earpiece 12 designed to couple acoustically to the ear of a singer during use. The earpiece 12 comprises a body 13 having a flexible or malleable nipple 14 projecting from one side thereof. The nipple 14 is sized and configured to conform to and fit snuggly in the singer's ear canal in such a way that the ear canal is essentially plugged by the nipple and ambient sounds and noise are blocked or reduced substantially by the nipple. An ambient sound inlet 21 is formed in the opposite side of the body 13 from the nipple 14 and functions, as described in detail below, to admit a controlled amount of ambient sound to the singer's ear. A mixing baffle 22 is movably disposed in a slot 30 formed within the body 13 and can be selectively pivoted in the directions indicated by arrow 23 to admit varying amounts of ambient sounds to the singer's ear, also as detailed below.

An acoustic waveguide 16 is coupled to the body 13 at location 19 on its peripheral surface and extends therefrom to a generally open end 17. In this embodiment, the waveguide 16 is formed by a tubular member having an internal passageway 18 (FIG. 2), but may take on a variety of shapes and configurations if desired so long as it receives acoustic waves at its open end 17 and guides them along the length of the waveguide. In use, a singer dons the vocal monitor 11 by inserting the nipple 14 snuggly into his ear and adjusting the body 12 until the acoustic waveguide 16 extends along his cheek with the open end 17 located beside or adjacent his mouth. The acoustic vibrations of the singer's voice then impinge upon the open end 17 of the waveguide, which excites corresponding acoustic vibrations in the column of air within the waveguide. These acoustic vibrations, in tern, propagate through the waveguide and the canal of the earpiece to the singer's eardrum, as indicated at 43 in FIG. 2 and as described in more detail below.

Figure 2:
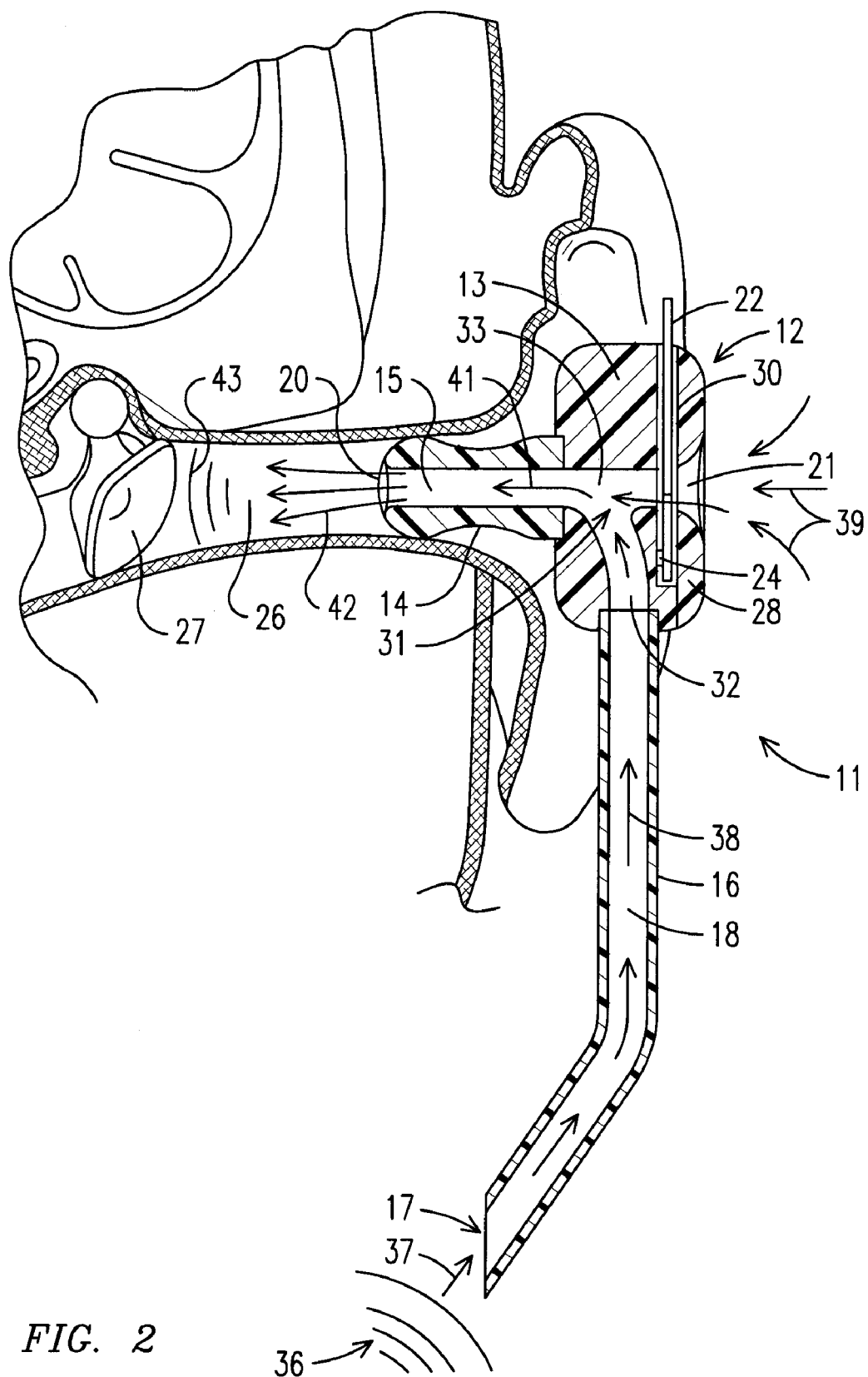
FIG. 2 is a cross sectional view of the passive personal vocal monitor of FIG. 1 illustrating one possible embodiment of internal passageways and canals within the monitor.

FIG. 2 is a cross-sectional view of the monitor of FIG. 1 illustrating one embodiment of internal features and configurations thereof. The body 13 is seen to be formed with an internal canal 31 that includes a first branch 32 and a second branch 33. The first branch 31 of the canal is acoustically coupled to the internal channel 18 of the acoustic waveguide 16. The second branch 33 of the canal is acoustically coupled at one end to the ambient sound inlet 21 of the body 13 and at its other end to an internal channel 15 that extends through the flexible nipple 14 to an open end 20. The nipple 14 is shown in FIG. 2 disposed snuggly within a singer's ear canal 26 with the open end 20 of the nipple 14 facing the singer's eardrum 27. The mixing baffle 22 is seen pivotally disposed in slot 30 and, in the position shown in FIG. 2, partially blocks the second branch 33 of the internal canal 31.

With continued reference to FIG. 2, when the singer sings, sound waves 36 from the singers mount impinge upon the open end 17 of the acoustic waveguide 16 located adjacent to or beside the mouth as indicated at 37. This excites the column of air within the waveguide creating sound or pressure wave patterns corresponding to those of the original sound wave. These sound wave patterns propagate along the internal channel 18 of the acoustic waveguide as indicated by arrows 38 and ultimately enter the internal canal 31 of the earpiece body 13. The sound wave patterns are then directed along the first branch 32 of the canal 31 and into the internal channel 15 of the nipple 14, as indicated at 41. The sound wave pressure patterns then exit the open end 20 of the channel 15 to impinge upon and excite the eardrum 27 of the singer. Thus, the sounds of the singer's voice are transmitted at the speed of sound from the singer's mouth to the singer's ear in such a way that the singer can hear his own voice clearly, even when immersed in high levels of ambient sounds and noises.

It has been found that in some situations, such as when singing in a band and surrounded by instruments, it is helpful for the singer also to hear some of the instrument sounds along with his own voice. In these situations, ambient sounds 39 impinge upon the ambient inlet 21 of the body 13 to excite the short column of air therein. If the singer wishes to hear more of these ambient sounds he may pivot the mixing baffle 22 rearwardly to expose all or a portion of the second branch 33 of the canal 31 to the ambient inlet 21. In this way, the sound pressure waves impinging upon the inlet 21 can propagate from the inlet into the second branch 33 of the canal, from where they propagate down the canal mix with the sound waves created by the singer's voice, and ultimately project from the end 20 of the nipple's internal passageway 15 to impinge upon the singer's ear. The singer thus hears a mixture of his own voice and the ambient sounds around him.

Further, the singer can create a custom mix of these ambient sounds and his voice by adjusting the position of the mixing baffle 22. Specifically, pivoting the mixing baffle rearward opens up the ambient inlet more and increases the level of ambient sounds heard by the singer relative to his voice. Alternatively, pivoting the baffle forward closes down the ambient inlet thus reducing the level of ambient sounds heard by the singer relative to his voice. This custom mix can be created and adjusted in real time by the singer himself to insure that the mix of ambient sounds and voice are optimized for the singer so that songs can be performed in key and with the proper dynamic inflections.

FIG. 3 illustrates better the function of the mixing baffle 22 in the illustrated embodiment. The cap 28 has been removed from the body 13 in this figure to reveal the mixing baffle 22 disposed within its slot 30. More specifically, the mixing baffle 22 is seen to be pivotally attached by a pivot pin 24 to the body 13 so that it can pivot backward and forward within the slot 30 as indicated by arrow 23. The mixing baffle 22 has an edge 46 that moves across the opening of the second branch 33 of the canal as the baffle is manipulated. In FIG. 3, the mixing baffle is positioned so that the ambient inlet is partially open to the canal to admit a portion of the ambient sounds to be mixed with a singer's voice. The mixing baffle may be pivoted completely rearward to admit the most ambient sound or completely forward to admit the least. Thus, as mentioned, creating a custom mix is a simple matter of adjusting the mixing baffle 22 in real time.

While not shown in the drawings, the open end 17 of the waveguide 16 may be covered with or coupled to a vibratory diaphragm to isolate the column of air within the waveguide from ambience. Sound pressure waves from the singer's voice then impinge upon the diaphragm, which in turn is caused to vibrate thereby exciting the enclosed column of air within the waveguide. This creates corresponding sound pressure waves in the column of air in the waveguide while maintaining the isolation of the air column. Isolation of the column may improve performance by decreasing the level of ambient sounds entering the waveguide through its open end, decreasing plosives, and reducing the impact of a blowing wind at the otherwise open end of the acoustic waveguide.

The invention has been described herein in terms of preferred embodiments and methodologies considered by the inventor to represent a best mode of carrying out the invention. Clearly, however, a wide variety of modifications and substitutions might be made by the skilled artisan within the scope of the invention. For example, the particular shape of the earpiece, the acoustic waveguide, and the nipple are not at all limiting and these components may take on virtually any shape as dictated by form or function. The various channels and canals can be changed in configuration and dimension. For example, the internal canal within the ear piece may be made gradually smaller or larger as it approaches the channel of the nipple to concentrate or otherwise enhance or change the nature of the sound pressure waves transmitted to the singer's ear. The components of the monitor may be smaller and/or larger than illustrated and may be made of any appropriate materials or combinations of materials as needed. In this regard, plastics and/or rubbers, and/or various polymers are considered to be preferred; although metals also may be used for components of the monitor. These and other additions, deletions, and changes might well be made by those of skill in the art without departing from the spirit and scope of the invention as set forth in the claims.

What is claimed is:

1. A passive personal vocal monitor having no electronic components, the monitor comprising:
   an earpiece having a nipple configured to fit within the ear of a user;
   a passageway in the nipple having a generally open end located adjacent a user's eardrum when the nipple is within the ear of the user;
   a generally tubular acoustic waveguide connected to the earpiece and extending therefrom to a generally open end positionable adjacent a user's mouth when the nipple is within the ear of the user; and
   an internal canal within the earpiece acoustically coupling the acoustic waveguide to the passageway in the nipple;
   sound pressure waves corresponding to the sound of the user's voice being conveyed along the acoustic waveguide, through the internal canal, through the passageway in the nipple, and to the user's eardrum to allow the user to hear the sound of his voice while performing.

2. A passive personal vocal monitor as claimed in claim 1 and further comprising an ambient sound inlet in the body acoustically coupled to the internal canal to admit ambient sounds into the canal to be mixed with the sounds of a user's voice.

3. A passive personal vocal monitor as claimed in claim 2 and further comprising an adjustable mixer on the body for varying the level of ambient sounds mixed with the sounds of a user's voice.

4. A passive personal vocal monitor as claimed in claim 3 and wherein the mixer comprises a mixing baffle selectively movable between a first position substantially blocking the ambient sound inlet and a second position substantially opening up the ambient sound inlet.

5. A passive personal vocal monitor as claimed in claim 1 and wherein the nipple is flexible.

6. A passive personal vocal monitor as claimed in claim 5 and wherein the nipple is configured to plug substantially a user's ear canal when disposed therein to minimize unwanted ambient sounds admitted to the user's ear.

7. A passive personal vocal monitor as claimed in claim 1 and wherein the earpiece is made substantially of plastic.

8. A passive personal vocal monitor as claimed in claim 7 and wherein the acoustic waveguide is made substantially of plastic.

9. A vocal monitor comprising a first portion configured to be inserted into a user's ear and having an internal channel terminating adjacent the user's eardrum, a second portion having an end positioned adjacent the user's mouth when the first portion is in the user's ear, the second portion having an internal channel terminating at the end, the internal channel of the first portion being acoustically coupled without electronic components to the internal channel of the second portion for conveying sound pressure waves from the vicinity of the user's mouth to the user's eardrum to allow the user to hear his voice clearly.

10. A vocal monitor as claimed in claim 9 and further comprising an ambient sound inlet for admitting ambient sound.

11. A vocal monitor as claimed in claim 10 and wherein the ambient sound inlet is acoustically coupled to the internal channel of the first portion to admit ambient sounds to be mixed with sounds of the user's voice.

12. A vocal monitor as claimed in claim 11 and further including a mixer for varying the level of ambient sounds mixed with the sounds of a user's voice.

13. A vocal monitor as claimed in claim 12 and wherein the mixer comprises a mechanism for selectively blocking and unblocking the ambient sound inlet.

14. A vocal monitor as claimed in claim 13 and wherein the mechanism is a baffle.

15. A vocal monitor as claimed in claim 13 and wherein the mechanism may be positioned to block the ambient sound inlet partially to admit a portion of ambient sounds.

16. A device for enhancing the sound of a user's voice to the user, the device comprising an earpiece insertable in the user's ear and having a channel terminating in an open end adjacent the user's eardrum, a tubular waveguide extending from the earpiece to an end that is positionable adjacent the user's mouth when the earpiece in the user's ear, the tubular waveguide being acoustically coupled without electronic components to the channel to capture sounds of the user's voice at the end of the tubular waveguide and convey corresponding sound pressure waves through the channel and to the user's eardrum.

17. The device of claim 16 and further comprising an ambient sound inlet acoustically coupled to the channel for admitting ambient sounds to be mixed with the sounds of the user's voice.

18. The device of claim 17 and further comprising means for adjusting the level of ambient sounds admitted.

19. The device of claim 18 and wherein the means for adjusting comprises a mixing baffle movable progressively between a first position substantially blocking the ambient sound inlet and a second position substantially opening up the ambient sound inlet.

* * * * *